United States Patent [19]

Hoshowski et al.

[11] Patent Number: 5,137,715

[45] Date of Patent: Aug. 11, 1992

[54] HAIR SHAMPOO-CONDITIONER COMPOSITION

[75] Inventors: Myra A. Hoshowski, Addison; William J. Brown, Flossmoor, both of Ill.

[73] Assignee: Helene Curtis, Inc., Chicago, Ill.

[21] Appl. No.: 623,788

[22] Filed: Dec. 7, 1990

[51] Int. Cl.$^5$ .............................................. A61K 7/06
[52] U.S. Cl. .................................... 424/70; 424/78.02; 252/DIG. 13
[58] Field of Search .................... 424/70, 78; 252/DIG. 13

[56] References Cited

U.S. PATENT DOCUMENTS

| | | | |
|---|---|---|---|
| 3,980,769 | 9/1976 | Ghilardi et al. | 424/70 |
| 3,996,146 | 12/1976 | Tarasov et al. | 424/70 X |
| 4,172,887 | 10/1979 | Vanlerberghe et al. | 424/70 |
| 4,213,960 | 7/1980 | Grollier et al. | 424/70 X |
| 4,240,450 | 12/1980 | Grollier et al. | 424/72 X |
| 4,710,374 | 12/1987 | Grollier et al. | 424/70 X |
| 4,842,851 | 6/1989 | Grollier et al. | 424/70 X |
| 4,948,576 | 8/1990 | Verdicchio et al. | 424/70 X |

Primary Examiner—Thurman K. Page
Assistant Examiner—D. Colucci
Attorney, Agent, or Firm—Marshall, O'Toole, Gerstein, Murray & Bicknell

[57] ABSTRACT

A hair shampoo-conditioner composition including an anionic cleansing surfactant, such as an alkyl sulfate or an alkyl ether sulfate, and a polymeric conditioning compound having the formula:

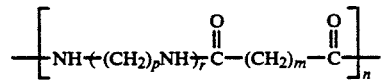

wherein n is a number in the range of from two to about 1000; m is a number in the range of from one to about 18; p and r are numbers in the range of from one to about four, in a suitable carrier, and having a pH of from about 2.5 to less than 7, to cleanse the hair, to generate a copious and stable foam volume and to impart improved wet stage and improved dry stage conditioning properties to the hair in a single application of the composition is disclosed.

26 Claims, 3 Drawing Sheets

HAIR SHAMPOO-CONDITIONER COMPOSITION

FIELD OF INVENTION

The present invention relates to a hair shampoo-conditioner composition and to a method of treating hair that generates a stable and copious foam, that cleanses the hair and that imparts improved wet stage and improved dry stage conditioning properties to hair in a single application of the composition. More particularly, the present invention is directed to a hair shampoo-conditioner composition including: a) an anionic cleansing surfactant, like an alkyl ether sulfate, such as sodium lauryl ether sulfate, or an alkyl sulfate, such as ammonium lauryl sulfate; b) a polymeric cationic conditioning compound having the formula:

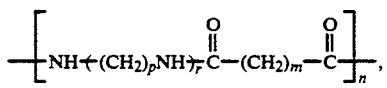

wherein r is a number in the range of from two to about 1000, and preferably in the range of from two to about 500; m is a number in the range of from one to about 18; p and r are numbers in the range of from one to about four; in c) a suitable carrier; and adjusted to a pH of from about 2.5 to less than 7. The hair shampoo-conditioner composition demonstrates exceptional foaming properties, effectively cleanses the hair, and, simultaneously, imparts unexpectedly improved wet stage and dry stage conditioning properties to hair in a single application of the composition. Surprisingly, a hair shampoo-conditioner composition of the present invention generates an unexpectedly high level of a stable foam. In addition, the anionic component and the cationic component of the composition do not interact, and therefore are available to effectively cleanse the hair and to impart wet stage and dry stage conditioning properties to the hair.

BACKGROUND OF THE INVENTION

Most individuals buy and use a hair shampoo for its cleansing properties. Furthermore, in addition to clean hair, the consumer desires sufficiently-conditioned hair that holds a preset configuration. However, present-day hair shampoos generally are formulated with highly-effective synthetic surfactants, like anionic surfactants, that exhibit a high foam and primarily clean, as opposed to conditioning, the hair Therefore, it is not surprising that hair shampoos neither help detangle wet hair nor impart any residual hair conditioning benefits to dry hair, such as the manageability or styleability of hair sets.

Consequently, after shampooing, the hair normally is left in a cosmetically-unsatisfactory state because an anionic surfactant-based hair shampoo composition not only removes all of the dirt and soil from the hair, but also removes essentially all of the sebum that is naturally present on the surface of the hair fibers. Therefore, it was found that the properties of anionic surfactants that effectively cleanse the hair also serve to leave the hair in a cosmetically-unsatisfactory condition. In general, therefore, shampooing the hair with a hair shampoo composition including an anionic surfactant, or a nonionic surfactant or an amphoteric surfactant, leaves the hair, after rinsing with water, with an undesirable harsh, dull and dry touch or feel, usually called "creak".

As a result, thoroughly cleansed hair is extremely difficult to comb, in either the wet or dry stage, because the individual hair fibers tend to snarl, kink, and interlock with each other. In addition, incompletely dried hair, such as hair dried with a towel, has poor brushing properties. Then, after complete drying, the hair does not set well. Furthermore, the combing or brushing property of the dried hair remains poor. The dried hair also has undesirable electrostatic properties in a low humidity atmosphere that cause the hair to "fly away", thereby further reducing the brushing property of the hair. The unsatisfactory combing or brushing property of freshly-shampooed hair also causes hair damage, such as split ends or hair breakage. In addition, the natural luster and resiliency of the hair is reduced.

Accordingly, freshly-shampooed hair usually requires a post-shampoo hair treatment with a conditioning composition to improve the unsatisfactory physical and cosmetic condition of the hair. A conditioning composition normally is applied separately from the hair shampoo, and usually is a rinse or a cream-like lotion containing a cationic compound. Therefore, investigators have sought hair shampoo compositions that generate a copious and stable amount of foam, cleanse the hair and leave the hair in a cosmetically-satisfactory state, such that the subsequent treatment with a conditioner composition can be avoided.

Consequently, investigators sought a composition that behaves both as a shampoo and as a hair conditioner. However, the resulting shampoo-conditioner compositions possessed several disadvantages. For example, it is known in the art that anionic surfactants generate a high foam and are suitable for cleansing the hair, and that, in many instances, cationic compounds, like cationic surfactants and polymers, are suitable hair conditioners. However, the major difficulty encountered by investigators is the inherent incompatibility between an anionic surfactant and a cationic surfactant or cationic polymer. Consequently, contact between the anionic surfactant and the cationic surfactant or cationic polymer either produces an intractable precipitate that forms immediately, or causes an interaction between the anionic and cationic components that significantly reduces their respective foam generating, cleansing and conditioning properties. The reduction in foaming, cleansing and conditioning effectiveness also is observed in compositions wherein the anionic and cationic components do not precipitate from the composition, but remain in solution or in a suspended state.

The inherent incompatibility between an anionic compound and a cationic compound is well recognized by workers skilled in the art. For example, Sagarin in *Cosmetics*, Interscience Publishers, Inc., New York, p. 538, 1957, states that anionic and cationic compound cannot be used in combination because they react to form insoluble salts. Thus, in practice, consumer needs traditionally have been met by applying a high-foaming and nonsubstantive anionic surfactant-based shampoo to the hair to cleanse the hair, then rinsing the hair, followed by applying a conditioner composition including a substantive cationic compound to the hair to condition the hair.

As previously discussed, freshly-shampooed hair, being inclined to knot and tangle, is difficult to manage and comb. The wet combing problem has been solved by treating freshly-shampooed hair with a conditioner composition that includes a compound to coat the hair shaft and cause the individual hair shafts to resist tangling and matting because of conditioner compound residue on the hair shaft. Until recently the desirable properties of both a hair shampoo and a hair conditioner composition could not be incorporated into a single composition. Therefore, a shampoo composition and a conditioner composition were applied sequentially to achieve the benefits provided by each composition. Investigators attempting to combine all, or some, of the beneficial properties of a shampoo composition and of a conditioner composition into a single shampoo-conditioner composition concentrated particularly on incorporating the properties of a post-shampoo conditioning rinse into a hair shampoo composition.

Therefore, because hair shampoo compositions are predominantly anionic in character, the incorporation of a substantive cationic compound into an anionic shampoo composition ranges from difficult to impossible because of the inherent incompatibility between anionic and cationic surfactants. Nevertheless, a combination shampoo-conditioner composition is desirable because of the convenience such a combination product offers to the consumer. In such a shampoo-conditioner product, the anionic surfactant acts to rid the hair and scalp of dirt, surface film, debris, and the like, while the cationic compound deposits on the hair to provide conditioning benefits, such as manageability, shine and texture. However, until the composition and method of the present invention, it has proven difficult to provide a stable hair shampoo-conditioner composition because of the inherent incompatibility between cationic and anionic surfactants. Consequently, and in accordance with an important feature of the present invention, a polymeric cationic conditioning compound is incorporated into a composition wherein an interaction between the anionic and cationic components of the composition is essentially precluded. The hair shampoo-conditioner composition then is utilized to cleanse the hair and, simultaneously, to impart conditioning properties to the hair. In addition, the composition generates a copious and stable foam level that usually is demonstrated only by a hair shampoo composition absent a conditioning compound.

Therefore, the need for an effective and stable shampoo-conditioner composition that cleanses the hair and conditions the hair, i.e., renders the hair more manageable, in a single hair treatment has long been recognized in the art. Accordingly, although conditioning compositions for application to previously-shampooed hair are well known, only recently have shampoo-conditioner compositions become available. For example, some shampoo-conditioner compositions are specially formulated for mildness, and accordingly low detergency, in order to leave a portion of the natural oils on the hair shaft. However, hair treated with this type of composition becomes greasy, dirty looking and dirty feeling relatively quickly.

Another type of shampoo-conditioner composition includes an oily component, such as a polyglycol, a glycol ester of a fatty acid, a natural or synthetic wax or a lanolin derivative, that is deposited on the hair during shampooing. However, the oily nature of such components reduces shampoo lathering and contributes to the feeling of greasy, dirty hair relatively soon after shampooing. Another type of shampoo-conditioner composition includes a substantive cationic polymer that deposits on the hair shaft during shampooing to impart the desired degree of manageability. However, the cationic polymers utilized in the prior art also gave the hair a greasy feeling as described above. The primary difficulty encountered in preparing this type of shampoo-conditioner composition has been achieving a sufficiently stable composition without destroying the delicate balance of conditioning, cleansing, consumer appeal, foam properties, and other functional and esthetic properties. Surprisingly and unexpectedly, although the composition of the present invention includes a polymeric cationic conditioning compound, the composition is sufficiently stable, lathers sufficiently, cleanses the hair and imparts conditioning properties to the hair without a greasy feeling, while maintaining excellent physical and esthetic properties for consumer appeal.

Therefore, the present invention relates to a shampoo-conditioner composition for cleansing the hair and for imparting improved physical and cosmetic properties to the hair, such as improved combing properties, luster and manageability. It is known that anionic surfactants are especially useful for shampooing the hair and for generating a copious and stable foam level, and that cationic surfactants and cationic polymers are especially useful for conditioning the hair. In addition, combining an anionic surfactant and a cationic compound in a shampoo-conditioner composition has proven difficult because of the inherent chemical incompatibility between the two classes of surfactants. Consequently, and in accordance with the present invention, it has been found that anionic surfactants can be combined with a particular polymeric cationic conditioning compound to provide a stable and effective hair shampoo-conditioner composition. The composition is sufficiently stable to resist phase separation during storage and effectively resists an interaction between the cationic and the anionic components of the composition; but, upon application to the hair, sufficiently deposits a substantial amount of the polymeric cationic conditioning compound onto the hair to withstand rinsing from the hair during the shampooing and rinsing process.

More particularly, it has been found that a polymeric cationic conditioning compound having the formula:

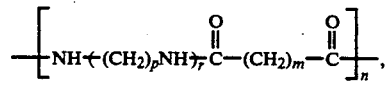

wherein n is a number in the range of from two to about 1000, and preferably from two to about 500; m is a number in the range of from one to about 18; and p and r are numbers in the range of from one to about four, when incorporated into a shampoo composition including a nonsubstantive anionic cleansing surfactant, provides a hair shampoo-conditioner composition that generates a copious and stable foam level and thoroughly cleanses the hair, in addition to depositing a sufficient amount of the cationic polymer onto the hair to condition the hair without demonstrating a greasy feeling. Such results are unexpected in the art because anionic surfactants, as a class, often are incompatible with a cationic polymer, and, if compatible, demonstrate a substantially reduced ability to generate foam. Therefore, the compatibility demonstrated by the combination of the anionic cleansing surfactant and the cationic conditioning polymer utilized in the present invention is both new and surprising, thereby permitting sufficient deposition of the substantive cationic conditioning compound onto the hair, while the anionic cleansing surfactant generates a consumer-acceptable foam level and shampoos the hair.

Overall, cationic compounds, such as cationic surfactants and cationic polymers, are known to be substantive to human hair and traditionally are used to complete the hair cleansing and hair conditioning cycle. The ability of a cationic compound to interact with the keratinous material of hair makes cationic compounds the most widely used compounds to impart the desired physical and cosmetic conditioning properties, such as wet hair detangling and dry hair manageability, to hair. Most commonly, the cationic compounds are applied to freshly shampooed and rinsed hair from a post-shampoo conditioning rinse. More recently, investigators have incorporated the cationic compound into anionic surfactant-based hair shampoos by carefully balancing the composition components to reduce or avoid an interaction between the cationic compounds and the anionic surfactants.

Cationic compounds that have been incorporated into anionic hair shampoo compositions include, for example, water-soluble proteins or protein degradation products, or polycationic polymers, such as the amino polycarbamide resins of the type described in DE-OS No. 21 50 899; polycationic cellulose derivatives of the type described in U.S. Pat. No. 3,816,616; or polycationic guar derivatives of the type described in U.S. Pat. No. 4,292,212. Many other water-soluble polymers containing cationic or quaternary ammonium groups have been proposed for use in an anionic surfactant-based hair shampoo. However, even though particular cationic compounds, especially particular cationic polymers, are compatible with anionic surfactants, a disadvantage common to all cationic hair conditioning compounds is that at least a partially-reduced conditioning effect and a substantially-reduced foam generating ability is observed when the cationic compound is included in an anionic surfactant-based hair shampoo. In contrast, and as will be demonstrated more fully hereinafter, the hair shampoo-conditioner compositions of the present invention generate a copious and stable foam, effectively cleanse the hair and impart conditioning properties to hair equivalent to properties imparted by a post-shampoo conditioner composition.

Accordingly, the present invention is directed to a hair shampoo-conditioner composition, including a nonsubstantive and high-foaming anionic cleansing surfactant and a polymeric conditioning compound, that simultaneously cleanses the hair and imparts desirable physical and cosmetic properties to the hair. By treating the hair with the shampoo-conditioner composition of the present invention, the hair is easily-combed when wet and the hair possesses satisfactory cosmetic properties when dry, including, in particular, elasticity, body, sheen and manageability. In contrast to the prior art, wherein cationic polymers were blended primarily with amphoteric surfactants, the hair shampoo-conditioner composition of the present invention includes a particular polymeric conditioning compound to condition the hair and an anionic surfactant to cleanse the hair. In addition, the stability and incompatibility problems normally encountered when a cationic compound and anionic surfactant are present in the same composition have been overcome.

Previous attempts to provide a combination shampoo-conditioner composition include the disclosure of Goff in U.S. Pat. No. 2,950,255, wherein relatively small, equimolar amounts of an anionic surfactant and a monomeric quaternary ammonium surfactant are included in a hair shampoo based primarily on amphoteric and nonionic surfactants. Amphoteric and nonionic surfactants are mild detergents and are compatible with cationic surfactants, but are not as effective in generating foam or in cleansing the hair as anionic surfactants. Similarly, Anguillo et al., in U.S. Pat. No. 3,816,616, discloses the use of a guar gum-based cationic polymer in an anionic surfactant-based shampoo to provide a combination hair shampoo-conditioner composition. The compositions disclosed by Anguillo et al. were found to clean efficiently but are inefficient in imparting conditioning properties to the hair.

Gerstein, in U.S. Pat. No. 3,990,991, discloses a hair shampoo-conditioner composition comprising major amounts of an amphoteric surfactant and an ethoxylated or propoxylated cryptoanionic surfactant, with a minor amount of a cationic surfactant or cationic polymer. U.S. Pat. No. 4,061,602 to Oberstar et al. discloses a conditioning shampoo composition, comprising an amphoteric surfactant, an anionic surfactant and a cationic derivative of a naturally-occurring polymer, that cleans and imparts conditioning properties to the hair. Koehler et al. in U.S. Pat. No. 4,273,760 discloses a hair conditioning shampoo including a cationic polymer, an anionic surfactant and a nonionic surfactant that conditions and cleanses the hair Barker in U.S. Pat. No. 4,247,538 discloses a conditioning shampoo comprising an amphoteric surfactant base, a cationic surfactant and an anionic macrocolloid polymer. Cseh, in U.S. Pat. No. 4,676,978, discloses a conditioning shampoo that includes a polycationic guar derivative, a hardenable cationic polycondensation product, a nonionic surfactant, and a film-forming polymer in an anionic surfactant-based shampoo. Scandel, in U.S. Pat. No. 4,832,872, teaches a hair shampoo-conditioner including an anionic surfactant, a conditioning amine oxide, and a conditioning cationic quaternary polymer.

Homma et al., in U.S. Pat. No. 4,381,259, disclose a hair shampoo-conditioner composition comprising a surfactant effective for washing hair, an anionic phosphoric acid ester surfactant and a cationic polymer. Specifically, Homma et al. disclose, at column 4, lines 37-39, that a suitable cationic polymer is a copolymer of adipic acid and dimethylaminohydroxypropylene diethylenetriamine. This polymer differs from the polymer utilized in the present invention in that a nitrogen atom of the diethylenetriamine is substituted with a propylene moiety including a hydroxy substituent and a dimethylamino substituent. The copolymer utilized in the present invention does not include a substituent on a nitrogen atom of the polyamine. Further, the composition and method of the present invention do not require an anionic phosphate ester surfactant to generate a sufficient foam volume, to cleanse the hair or to impart conditioning properties to the hair.

The following additional patents and publications also are directed to hair shampoo-conditioner compositions and compounds used in hair shampoo-conditioner compositions: A. Hunting, "The Function of Polymers in Shampoos and Conditioners", *Cosmet. Toiletries*, 99(6), 57-60, 1984; Coney, U.S. Pat. No. 3,793,210; Olson, Jr. et al., U.S. Pat. No. 3,697,452; Hewitt, U.S. Pat. Nos. 3,755,559, 3,849,348 and 3,642,577; Tarasov et al., U.S. Pat. No. 3,996,146; Birkofer, U.S. Pat. No. 3,926,840; Barker U.S. Pat. No. 3,668,136. The prior art teaching that an amphoteric detergent is necessary in a shampoo-conditioner composition is exemplified by the following patents directed to conditioning shampoos U.S. Pat. Nos. 3,313,734; 3,962,418; 2,999,069; 3,055,836; 3,996,146; 4,009,256 and 3,400,198. These patents, and others, teach the necessity of including an amphoteric or polar nonionic component in the composition to achieve compatibility between the cationic conditioning compound and the remaining components of the shampoo formulation.

Forestier et al., in U.S. Pat. No. 4,866,159, disclose the use of a polyaminoamide in a skin care or a hair care product to filter ultraviolet radiation, and therefore to protect the skin or hair from harmful solar radiation. Forestier et al. specifically disclose a crosslinked polyaminoamide including a condensation product of a dicarboxylic acid and a polyamine partially substituted with an ultraviolet radiation absorbing moiety. The substituted condensation product is incorporated into a skin care or a hair care composition in a sufficient amount to protect the treated skin or hair from ultraviolet radiation. The Forestier et al. disclosure does not teach or suggest the use of a substantially uncrosslinked, unsubstituted copolymer of a dicarboxylic acid and polyamine as a hair-conditioning compound that does not adversely affect the ability of an anionic surfactant-based composition to generate a stable and copious foam volume.

As will be shown in the following detailed description of the invention, these references fail, singly or in combination, to anticipate or suggest the composition and method of the present invention, wherein a polymeric conditioning compound is combined with an anionic cleansing surfactant, at a pH of from about 2.5 to less than 7, to provide a sufficiently stable hair shampoo-conditioner composition that effectively, and simultaneously, generates a copious and stable foam volume, cleanses the hair and imparts improved conditioning properties to the hair. Surprisingly, the composition of the present invention is sufficiently stable to resist phase separation even though both an anionic surfactant and a cationic component are present in the composition. Furthermore, the composition demonstrates a superior ability to generate a thick, stable lather and to deposit the conditioning agent on the hair without exhibiting an excessive build-up of the polymeric conditioning compound on the hair shaft after repeated shampooings.

Therefore, and in accordance with the present invention, the hair is cleansed and, simultaneously, excellent hair conditioning properties are imparted to the hair by a method of contacting the hair with a composition comprising an anionic cleansing surfactant and a particular polymeric conditioning compound, and having a pH of from about 2.5 to less than 7. Consequently, the method of the present invention provides a copious and stable foam, and both cleanses the hair and conditions the hair to provide more manageable and esthetically-pleasing hair in a single application of the shampoo-conditioner composition to the hair.

SUMMARY OF THE INVENTION

In brief, the present invention is directed to a composition and method of simultaneously shampooing and conditioning hair. More particularly, the present invention relates to a method of treating the hair, whereby the hair is cleansed and conditioned, simultaneously, by contacting the hair with a composition comprising an anionic cleansing surfactant and a polymeric conditioning compound having the general structural formula (I):

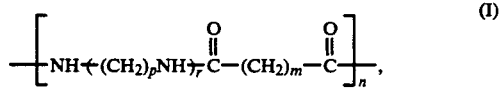

wherein n is a number in the range of from two to about 1000, and preferably in the range of from two to about 500; m is a number in the range of from one to about 18; and p and r are numbers in the range of from one to about four; in a suitable carrier. Optionally, a nonionic surfactant, like an alkanolamide; an amphoteric surfactant, like a betaine or a hydroxysultaine; or a combination thereof, can be included in the composition to improve the esthetic properties and consumer appeal of the composition.

Consequently, treating the hair with single application of an aqueous composition including an anionic cleansing surfactant, such as an alkyl ether sulfate, like sodium lauryl ether sulfate; and a substantially uncrosslinked polymeric conditioning compound having general structural formula (I), like a copolymer of adipic acid and diethylenetriamine, provides a copious and stable lather, effectively cleanses the hair and simultaneously imparts excellent wet stage and excellent dry stage conditioning properties to the hair. Surprisingly and unexpectedly, hair treated with an easy-to-apply shampoo-conditioner composition of the present invention is thoroughly cleansed and exhibits improved physical and cosmetic properties, such as wet combing, dry combing, manageability, softness and body.

Therefore, in accordance with an important feature of the present invention, a hair-treating composition that cleanses the hair and imparts improved physical properties and cosmetic properties to the hair in a single application is provided. The hair-treating composition comprises an anionic cleansing surfactant and a polymeric conditioning compound of general structural formula (I) in a suitable carrier; and, optionally, a nonionic surfactant, an amphoteric surfactant or a combination thereof. The hair shampoo-conditioner composition of the present invention generates a copious, stable foam level and is capable of cleansing the hair and imparting improved physical and cosmetic conditioning properties to the hair over a pH range of from about 2.5 to less than 7.

The present invention also is directed to a method of treating hair comprising contacting the hair with a composition having a pH of from about 2.5 to less than 7, wherein the composition includes an anionic cleansing surfactant and a polymeric conditioning compound, like a copolymer of adipic acid and diethylenetriamine, in a suitable carrier, and, optionally, a nonionic surfactant, an amphoteric surfactant, or a combination thereof; rinsing the hair; then drying the hair, to cleanse the hair and simultaneously impart improved physical and cosmetic conditioning properties to the hair in a single application of the composition.

In accordance with another important feature of the present invention, a method of treating hair to yield cleansed and unexpectedly well-conditioned hair includes contacting the hair with an aqueous composition comprising from about 1% to about 20% by weight of an anionic cleansing surfactant, and from about 0.1% to about 2.5% by weight of a polymeric cationic conditioning compound having the general structural formula (I):

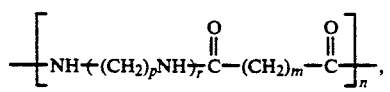

wherein n is a number in the range of from two to about 1000, and preferably in the range of from two to about 500, m is a number in the range of from about one to about 18, and p and r are numbers in the range of from one to about four; rinsing the hair; and then drying the hair.

In particular, the present invention is directed to providing a method of treating hair to yield, in a single hair treatment, cleansed and unexpectedly well-conditioned hair by contacting the hair with an aqueous composition comprising from about 1% to about 20% by weight of an anionic cleansing surfactant, like ammonium lauryl sulfate; from about 0.1% to about 2.5% by weight of a polymeric conditioning compound of general structural formula (I), like a copolymer of adipic acid and diethylenetriamine; and, optionally, from 0% to about 5% by weight of an alkanolamide as the nonionic surfactant, from 0% to about 5% by weight of an amphoteric surfactant, or a combination thereof; rinsing the hair; and then drying the hair. The new and improved hair shampoo-conditioner composition is capable of generating a copious and stable foam; effectively cleansing the hair; and of imparting improved physical, cosmetic and esthetic conditioning properties both to normal hair and to tinted, frosted, bleached or other substantially-damaged hair.

BRIEF DESCRIPTION OF THE DRAWINGS

The above and other objects and advantages and novel features of the present invention will become apparent from the following detailed description of the preferred embodiments illustrated in the accompanying figures that show the cleansing ability and the hair conditioning properties imparted to shampooed hair by using the method and composition of the present invention, wherein.

DETAILED DESCRIPTION OF THE INVENTION

Figure 1:
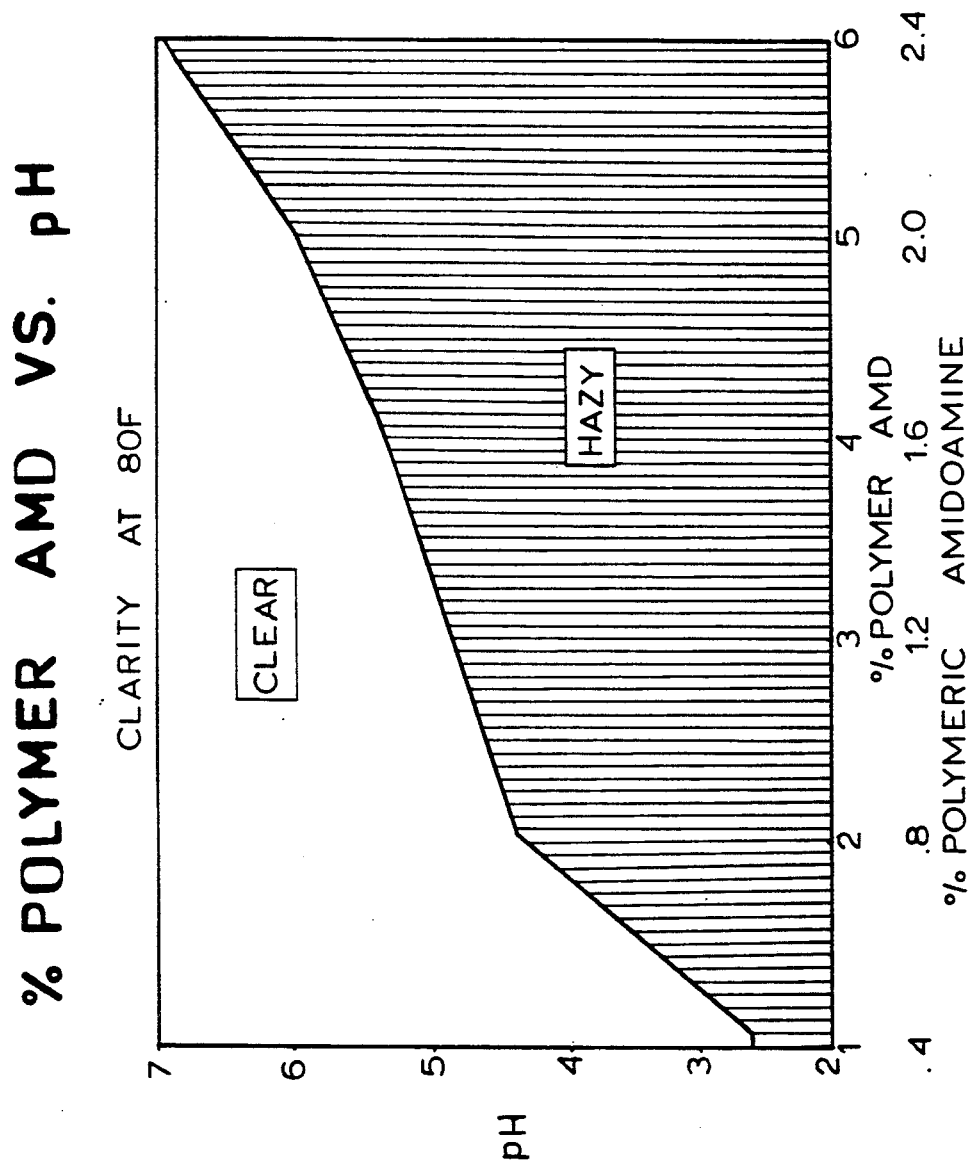
FIG. 1 is a graph of pH vs. percentage of polymeric amidoamine compound present in the hair shampoo-conditioner composition showing the minimum pH necessary to achieve a clear hair shampoo-conditioner composition.

The hair shampoo-conditioner composition of the present invention comprises an anionic cleansing surfactant and a polymeric conditioning compound in a suitable carrier. In accordance with an important feature of the present invention, the hair shampoo-conditioner composition includes a nonsubstantive, anionic cleansing surfactant and a substantive, polymeric conditioning agent to both cleanse and condition the hair in a single application of the composition to the hair, while, unexpectedly, generating a copious amount of stable foam. Surprisingly, the hair shampoo-conditioner composition of the present invention demonstrates excellent stability in regard to resisting phase separation and to resisting an interaction between the anionic and cationic components, thereby avoiding the necessity of including an amphoteric surfactant in the composition. An anionic surfactant is included in the composition to provide a shampoo-conditioner that generates a high volume of foam and most effectively cleanses the hair. However, optionally, an amphoteric surfactant or a nonionic surfactant, or a combination thereof, can be included in the composition to impart improved physical properties, and therefore provide enhanced consumer appeal, to the composition.

The easy-to-apply shampoo-conditioner composition not only effectively cleanses the hair and imparts excellent wet comb and dry comb conditioning properties to the hair, but unexpectedly provides foam levels typically not achieved in prior art shampoo-conditioner compositions. In general, the cleansed hair demonstrates improved physical and cosmetic conditioning properties, such as wet combing, dry combing, thickness, softness, manageability and body. As will be demonstrated more fully hereinafter, it is surprising and unexpected for a composition of the present invention, including an anionic cleansing compound and a polymeric conditioning compound, and having a pH in the range of from about 2.5 to less than 7, to generate such a high, stable foam level, to so effectively cleanse the hair and to impart such improved conditioning properties to the hair.

The anionic cleansing surfactant included in the composition and method of the present invention is selected from any of the anionic surfactants known or previously used in the art of hair shampoos. However, an anionic cleansing surfactant is an important ingredient in the composition of the present invention because the anionic surfactant effectively cleanses the hair and also generates a high, stable foam level that consumers equate with cleaning efficiency. Amphoteric and nonionic surfactants generally are not as effective in cleansing the hair and do not provide the high foam level desired by consumers. Therefore, amphoteric and nonionic surfactants are unsatisfactory as the primary cleansing surfactant in a composition of the present invention. However, optionally, an amphoteric or a nonionic surfactant can be included in a composition of the present invention, either alone or in combination with the anionic cleansing surfactant, to provide a suitable viscosity or to furnish other functional or esthetic properties to the composition.

Usually, the anionic cleansing surfactant includes a hydrophobic moiety, such as a carbon chain including from about eight carbon atoms to about 30 carbon atoms, and particularly from about twelve carbon atoms to about twenty carbon atoms; and further includes a hydrophilic moiety, such as sulfate, sulfonate, carbonate, phosphate or carboxylate. Often, the hydrophobic carbon chain is etherified, such as with ethylene oxide or propylene oxide, to impart a particular physical property, such as increased water solubility or reduced surface tension, to the anionic cleansing surfactant.

The anionic cleansing surfactants are well-known and have been widely used in the art of hair shampoos. Therefore, suitable anionic cleansing surfactants include, but are not limited to, compounds in the classes known as alkyl sulfates, alkyl ether sulfates, alkylamide sulfates, alkylamide ether sulfates, alkyl ether sulfonates, alkylamide sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, alkyl sulfosuccinates, alkyl ether sulfosuccinates, alkylamide sulfosuccinates, sarcosinates, alkyl phosphates, octoxynol or nonoxynol phosphates, taurates, fatty taurides, sulfated monoglycerides, fatty acid amido polyoxyethylene sulfates and isothienates; or combinations thereof. Many additional anionic cleansing surfactants are described in McCUTCHEON'S, DETERGENTS AND EMULSIFIERS, 1989 ANNUAL, published by McCutcheon Division, MC Publishing Co., and herein incorporated by reference.

Usually, the anionic cleansing surfactant is present in the composition as a neutralized salt in the form of a sodium, potassium, lithium, ammonium, alkylammonium or hydroxyalkylammonium salt, wherein the alkyl moiety includes from one to about three carbon atoms. The alkyl sulfates and alkyl ether sulfates are particularly effective classes of anionic cleansing surfactants. Consequently, exemplary anionic cleansing surfactants that are useful in the composition and method of the present invention include, but are not limited to, the ammonium, monoethanolamine, diethanolamine, triethanolamine, isopropylamine, sodium, potassium, lithium or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. Examples of especially useful anionic cleansing surfactants are a lauryl sulfate salt and a lauryl ether sulfate salt.

The anionic cleansing surfactant is present in the composition in an amount ranging from about 1% to about 20% by weight of the composition. It has been found that if the amount of an anionic cleansing surfactant in the composition is less than about 1% by weight, the hair is not sufficiently cleansed when contacted with a composition of the present invention. Furthermore, if the anionic surfactant is present in an amount greater than about 20% by weight, the composition is not adversely affected, but cleansing efficiency and foam generation is not further improved. Therefore, the extra amount of anionic surfactant is rinsed from the hair and wasted.

Accordingly, it has been found that the anionic cleansing surfactant is included in the hair shampoo-conditioner composition of the present invention in a preferred amount ranging from about 3% to about 15% by weight of the composition, and to achieve the full advantage of the present invention, from about 7% to about 12% by weight of the composition. Furthermore, surprisingly and unexpectedly, even when a low amount of anionic cleansing surfactant is included in the composition, the presence of the polymeric conditioning compound, even in its cationic form at a pH of from about 2.5 to less than 7, does not adversely affect the generation of an acceptable and stable foam level, thereby ensuring consumer acceptance.

In accordance with another important feature of the present invention, the hair shampoo-conditioner composition includes a polymeric conditioning compound that is substantive to the hair, imparts conditioning properties to the hair and does not adversely affect the level of foam generated by the anionic surfactant. The polymeric conditioning compound is a polymeric amidoamine compound, having general structural formula (I):

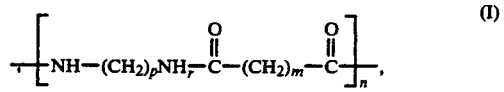

wherein n is a number in the range of from two to about 1000, and preferably in the range of from two to about 500; m is a number in the range of from one to about 18; and p and r are numbers in the range of from one to about four. To achieve the full advantage of the present invention, the compound of general structural formula (I) is a compound wherein n is a number in the range of from about 2 to about 300. Such an especially preferred amidoamine compound has an average molecular weight in the range of from about 240 to about 187,500. As illustrated, the polymeric amidoamine compound of general structural formula (I) is substantially uncrosslinked. At a pH of from about 2.5 to less than 7, the compound of general structural formula (I) is cationic in nature. This pH range is attained by neutralizing the polymeric amidoamine with a suitable acid.

The polymeric amidoamine compound is present in the hair shampoo-conditioner composition in an amount ranging from about 0.1% to about 2.5% by weight of the composition, and preferably in an amount ranging from about 0.15% to about 2.0% by weight of the composition. To achieve the full advantage of the present invention, the polymeric amidoamine is present in an amount ranging from about 0.2% to about 1.5% by weight of the composition. The polymeric amidoamine compound is included in the shampoo-conditioner composition to impart improved physical and cosmetic properties to the hair, and surprisingly, does not adversely affect the generation of a copious and stable foam level desired by consumers.

An example of a polymeric amidoamine compound having the general structural formula (I) that can be used in the composition and method of the present invention is the compound having the proposed CTFA designation adipic acid/diethylenetriamine copolymer, available commercially under the tradename POLYMER AMD from Sandoz, Inc., East Hanover, N.J., and having the structural formula (II):

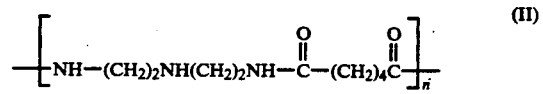

Other suitable polymeric amidoamine compounds include, but are not limited to, copolymers of a dicarboxylic acid and a polyamine. For example, a suitable dicarboxylic acid includes from about three to about twenty carbon atoms. Furthermore, the dicarboxylic acid can be aliphatic, aromatic, or include both aliphatic and aromatic moieties; or the polymeric amidoamine can include both an aromatic and an aliphatic dicarboxylic acid. It is envisioned that if the carbon chain length of an aliphatic dicarboxylic acid is appreciably above twenty, then the polymeric amidoamine may adversely affect the foam generating ability of the anionic cleansing surfactant and, if present, the optional amphoteric or nonionic surfactant. Accordingly, suitable aliphatic dicarboxylic acids that can be incorporated into the polymeric amidoamine compound of general structural formula (I) include, but are not limited to, malonic acid, succinic acid, maleic acid, fumaric acid, glutaric acid, adipic acid, pimelic acid, suberic acid, azelaic acid, sebacic acid and similar saturated and unsaturated dicarboxylic acids having from about 3 and up to about 20 carbon atoms; or combinations thereof. Similarly, suitable aromatic dicarboxylic acids that can be incorporated into the polymeric amidoamine compound of general structural formula (I) include, but are not limited to, phthalic acid, isophthalic acid, terephthalic acid, naphthalene-2,6-dicarboxylic acid, pyridine-2,5-dicarboxylic acid, quinoline-2,4-dicarboxylic acid, o-phenylenediacetic acid, m-phenylenediacetic acid, p-phenylenediacetic acid, homophthalic acid, o-phenyleneacetic-$\beta$-propionic acid, and similar dicarboxylic acids having up to about 20 carbon atoms and including an aromatic moiety; or combinations thereof.

In addition to the above dicarboxylic acids, various polyamines can be included in the polymeric amidoamine of general structural formula (I). For example, in addition to the diethylenetriamine illustrated in structural formula (II), the ethylene moiety can be replaced by any alkylene moiety including from one to about four carbon atoms, like, but not limited to, methylene, propylene, isopropylene, butylene, isobutylene and sec-butylene. Similarly the polyamine can include amino moieties only on its molecular ends, e.g. ethylenediamine, or can include amino moieties both on its molecular ends and interspersed throughout the carbon chain backbone, e.g. diethylenetriamine, triethylenetetramine, and dipropylenetriamine. Therefore, suitable polyamines include, but are not limited to, ethylenediamine, diethylenetriamine, triethylenetetramine, propylenediamine, dipropylenetriamine, 1,3-diaminopropane, 1,4-diaminobutane and combinations thereof. It also is envisioned that piperazine is a suitable polyamine to incorporate into the polymeric amidoamine of general structural formula (I).

In accordance with an important feature of the present invention, after neutralization with a suitable acid, an above-described polymeric amidoamine compound of structural formula (I) exhibits the properties of a cationic surfactant. Consequently, in the acid-neutralized state, the polymeric amidoamine compound behaves like a cationic surfactant, and therefore is substantive to the hair and imparts conditioning properties to the hair.

The acid used to neutralize the amidoamine compound essentially can be any organic acid or mineral acid of sufficient acid strength to neutralize a free amine nitrogen. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or combinations thereof. To achieve the full advantage of the present invention, the polymeric amidoamine compound is neutralized with citric acid. In general, a sufficient amount of acid is added to neutralize the polymeric amidoamine compound and to adjust the final pH of the hair-treating composition to within a range of from about 2.5 to less than 7; preferably in a pH range of from about 2.5 to about 6; and to achieve the full advantage of the present invention in a pH range of from about 2.5 to about 5.5.

As will be demonstrated more fully hereinafter, at a pH of less than about 2.5, the composition of the present invention can be an opaque composition, and the composition that does not generate a sufficient foam volume. At a pH of above about 2.5, such as up to a pH of about 11, a composition of the present invention is a clear composition that generates a stable and copious foam volume. However, in practice a hair shampoo composition or a hair shampoo-conditioner composition is adjusted to a pH of less than 7 to provide a composition that is non-irritating and nondamaging to the hair, skin and eyes of the consumer.

In addition to the above-described essential ingredients, other common cosmetic components and additives can be included in the composition of the present invention, as long as the basic properties of the hair shampoo-conditioner composition are not adversely affected. Such optional cosmetic additives and components include, but are not limited to, amphoteric surfactants, nonionic surfactants, fragrances, dyes, hair colorants, opacifiers, pearlescing agents, thickeners, dandruff control agents, hydrotropes, foam stabilizers, solubilizers, preservatives, water softening agents, acids, bases, buffers and the like. Likewise, the compositions can include other emulsifiers, conditioning agents, inorganic salts, humectants and similar materials to provide the composition with desirable esthetic or physical properties. These optional components and additives usually are present in weight percentages of less than about 5% by weight each, and usually from about 0.1% to about 20% by weight of the composition in total.

For example, to improve consumer acceptance, both skin mildness and enhanced composition esthetics can be achieved by optionally including an amphoteric surfactant in the hair shampoo-conditioner in an amount ranging from 0% to about 5% by weight of the composition. As stated previously, an anionic cleansing surfactant is an essential ingredient in the hair shampoo-conditioner composition to generate a sufficient foam level and to effectively cleanse the hair. To achieve the full advantage of the present invention however, both an anionic cleansing surfactant and an amphoteric surfactant are included in the shampoo-conditioner composition. Therefore, in addition to the anionic cleansing surfactant, the shampoo-conditioner composition of the present invention optionally can include an amphoteric surfactant. The amphoteric surfactant used in the method and composition of the present invention includes any of the amphoteric surfactants known or previously used in the art of hair shampoos, hair conditioners and hair shampoo-conditioners. Therefore, suitable amphoteric surfactants include, but are not limited to, compounds in the classes known as alkamphocarboxylates, alkamphopropylsulfonates, amine oxides, betaines, sultaines, aminopropionates and combinations thereof. Many additional amphoteric detergents are described in McCUTCHEON'S, DETERGENTS AND EMULSIFIERS, 1989 ANNUAL, published by McCutcheon Division, Mc Publishing Co., and herein incorporated by reference.

In particular, specific examples of amphoteric surfactants there can be used in the present invention include, but are not limited to, cocoamphoglycinate, cocoamphopropionate, cocoamphocarboxyglycinate, cocoamphocarboxypropionate, lauroamphoglycinate lauroamphocarboxypropionate, oleoamphopropionate, stearoamphoglycinate, caproamphocarboxyglycinate, caproamphoglycinate, caproamphocarboxypropionate, cocoamphopropylsulfonate, lauroamphopropylsulfonate, stearoamphopropylsulfonate, oleoamphopropylsulfonate, capryloamphopropylsulfonate, capryloamphoglycinate, capryloamphopropionate, capryloamphocarboxyglycinate, capryloamphocarboxypropionate, cocoamidopropyl betaine, lauramidopropyl betaine, oleamidopropyl betaine, coco betaine, oleyl betaine, cocamidopropyl hydroxysultaine, tallowamidopropyl hydroxysultaine, dihydroxyethyl tallow glycinate, lauraminodipropionate, tallowiminodipropionate, lauryl dimethyl amine oxide, myristyl dimethyl amine oxide, cetyl dimethyl amine oxide, cocamine oxide, stearyl dimethyl amine oxide, cocoamidopropyl dimethylamine oxide, tallow amine oxide, tallowamidopropyl dimethyl amine oxide and combinations thereof. In general, however, any amphoteric surfactant can be included in the composition of the present invention as long as the stability, the conditioning and the cleansing efficiency of the composition are not adversely affected.

The hair shampoo-conditioner compositions of the present invention also can include a nonionic surfactant to help impart esthetic, physical or cleansing properties to the composition. For example, representative nonionic surfactants that can be included in the hair shampoo-conditioner composition of the present invention include esters of polyols and sugars; fatty acid alkanolamides; polyethylene glycols; the ethoxylated or propoxylated alkylphenols; ethoxylated or propoxylated fatty alcohols; and the condensation products of ethylene oxide with long chain amides. These nonionic surfactants, as well as numerous other nonionic surfactants not cited herein, are well known in the art and are fully described in the literature, such as McCUTCHEON'S, DETERGENTS AND EMULSIFIERS, 1989 ANNUAL, published by McCutcheon Div., MC Publishing Co.

In particular, a nonionic alkanolamide can be included in the composition to provide composition thickening and foam stability. The alkanolamide can be included in an amount ranging from 0% to about 5% by weight of the composition. The alkanolamides are preferred thickeners because the usual organic thickeners used in cosmetics, such as sodium alginate; guar gum; xanthan gum; gum arabic; cellulose derivatives such as methylcellulose, hydroxybutylcellulose, hydroxyethylcellulose, hydroxypropylcellulose and carboxymethylcellulose; and various synthetic polymeric thickeners, such as the polyacrylic acid derivatives, have a tendency to decrease foam levels, whereas alkanolamides act to boost and stabilize foam levels. However, any of the above-listed thickeners can be included in the composition of the present invention. Accordingly, suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

The composition also can include optional conditioning agents and emulsifiers, like fatty alcohols including from about 12 to about 18 carbon atoms, such as myristyl alcohol, lauryl alcohol, stearyl alcohol, cetaryl alcohol or cetyl alcohol. Furthermore, fatty alcohols of about twelve to about eighteen carbon chain lengths that are ethoxylated or propoxylated can be used in place of the fatty alcohols themselves. Examples of such useful ethoxylated fatty acids include ethylene glycol cetyl ether, polyoxyethylene(2) stearyl ether, polyoxyethylene(24) cetyl ether, and the like; the exemplary compounds have CFTA Dictionary names of Ceteth-1, Steareth-2 and Ceteth-24, respectively. In general, the fatty alcohol conditioning agents, or other conditioning agents well-known to those skilled in the art, optionally can be included in the present hair shampoo-conditioner composition in an amount ranging from 0% to about 3% by weight of the composition, as long as the optional conditioning agent does not substantially affect the generation of a copious, stable foam.

The carrier of the hair shampoo-conditioner composition of the present invention is predominantly water, but nonaqueous solvents also can be included to help solubilize composition ingredients that are not sufficiently soluble in water, to adjust the viscosity of the composition or to act as a humectant. Suitable solvents include polyols, like glycerol; glycols, like ethylene glycol, propylene glycol and hexylene glycol; or mixtures thereof. The optional nonaqueous solvents should not adversely affect ability of the composition to generate a lather, to cleanse and condition the hair or otherwise adversely affect the consumer appeal of the composition. A nonaqueous solvent can be present in the hair shampoo-conditioner composition of the present invention in an amount ranging from 0% to about 5% by weight of the composition.

To achieve the full advantage of the present invention, the hair shampoo-conditioner composition is a relatively viscous mixture that is stable indefinitely at temperatures normally found in commercial product storage and shipping. A sufficiently viscous hair shampoo-conditioner composition results from a judicious selection of the anionic cleansing surfactant, the polymeric conditioning compound, and, if present, the optional nonionic surfactant, amphoteric surfactant or combination thereof. A composition of the present invention, either clear, opacified or pearlescent, is stable to phase separation and precipitation of composition ingredients at a temperature of about 20° C. to about 25° C. essentially indefinitely. The compositions also have demonstrated sufficient stability to phase separation and precipitation of ingredients at temperatures normally found in commercial product storage and shipping to remain unaffected for periods of one year or more.

In accordance with the method of the present invention, several hair shampoo-conditioner compositions were prepared, then applied to hair, to demonstrate the ability of a single application a composition, comprising an anionic cleansing surfactant and a polymeric conditioning compound, at a pH in the range of from about 2.5 to less than 7, to simultaneously cleanse the hair and impart hair-conditioning properties to the hair. Surprisingly, the present compositions generated greater and more stable foam levels than prior art hair shampoo-conditioners. It also has been demonstrated that a hair shampoo-conditioner composition of the present invention effectively imparts hair conditioning properties to the hair. Although the mechanism of interaction between the essential ingredients that provides a relatively stable composition capable of generating a copious foam and achieving a maximum deposition of polymeric conditioning compound on the hair is not known precisely, it has been theorized that the cationic functionalities of the acid-neutralized polymeric amidoamine compound and the anionic moieties of the cleansing surfactant are effectively isolated. Consequently, because contact between the anionic and cationic moieties present in the composition is effectively prevented, the cationic component is not precipitated from the composition, and does not otherwise interact with the anionic surfactant. Therefore, the polymeric conditioning compound, in its cationic form, is available to effectively deposit onto, and condition, the hair shaft. Similarly, the anionic cleansing surfactant also is available to effectively cleanse the hair. Furthermore, and as will be demonstrated more fully hereinafter, tests have shown both that copious and stable foam levels are generated during shampooing, thereby providing enhanced consumer appeal, even at the relatively low amounts of anionic cleansing surfactant present in the composition; and that excellent conditioning properties are imparted to the hair.

To demonstrate the new and unexpected results provided by the hair shampoo-conditioner of the present invention, the following Examples 1 through 9 were prepared. The composition of each Example was prepared by admixing the ingredients in the listed order, followed, if necessary, by a further addition of a citric acid solution to adjust the pH to a value between about 2.5 and less than 7. The composition of Examples 1 and 7 illustrate a shampoo formulation absent a conditioning agent. The composition of Examples 2 through 6, 8 and 9 illustrate either a composition of the present invention including a polymeric amidoamine of structural formula (II) (EXS. 2, 8 and 9) or a shampoo-conditioner composition including a prior art monomeric amidoamine conditioning agent (EXS. 3 through 6). Overall, the compositions of EXS. 2, 8 and 9 demonstrate the storage stability, the foam generating capabilities, the cleansing efficiency and conditioning properties imparted by a composition of the present invention. The weight percentages listed in the following examples represent the actual amount, by weight, of each ingredient present in the hair shampoo composition (EXS. 1 and 7) or the shampoo-conditioner composition (EXS. 2 through 6, 8 and 9).

| INGREDIENT (% by weight) | EX. 1 | EX. 2 | EX. 3 | EX. 4 | EX. 5 | EX. 6 | EX. 7 | EX. 8 | EX. 9 |
|---|---|---|---|---|---|---|---|---|---|
| Water, deionized | q.s. | q.s. | q.s. | q.s. | q.s. | q.s. | q.s. | q.s. | q.s. |
| Citric Acid[1] | q.s. to pH 4–6 | q.s. to pH 4–6 | q.s. to pH 4–6 | q.s. to pH 4–6 | q.s. to pH 4–6 | q.s. to pH 4–6 | q.s. to pH 4–6 | q.s. to pH 4–6 | q.s. to pH 4–6 |
| Ammonium Lauryl Sulfate[2] | 9.80 | 9.80 | 9.80 | 9.80 | 9.80 | 9.80 | — | — | — |
| Sodium Laureth-2 Sulfate[3] | — | — | — | — | — | — | 9.10 | 9.10 | 9.10 |
| Cocamide DEA | 2.50 | 2.50 | 2.50 | 2.50 | 2.50 | 2.50 | 2.50 | 2.50 | 2.50 |
| Cocamidopropyl Hydroxysultaine[4] | 1.75 | 1.75 | 1.75 | 1.75 | 1.75 | 1.75 | 1.75 | 1.75 | 1.75 |
| KATHON CG[5] | 0.05 | 0.05 | 0.05 | 0.05 | 0.05 | 0.05 | 0.05 | 0.05 | 0.05 |
| GLYDANT[6] | 0.20 | 0.20 | 0.20 | 0.20 | 0.20 | 0.20 | 0.20 | 0.20 | 0.20 |
| Sodium Chloride | 0.70 | 0.70 | 0.70 | 0.70 | 0.70 | 0.70 | 0.85 | 0.85 | 0.85 |
| Fragrance | 0.40 | 0.40 | 0.40 | 0.40 | 0.40 | 0.40 | 0.30 | 0.30 | 0.30 |
| Adipic Acid/ Diethylene- triamine Copolymer[7] | — | 0.20 | — | — | — | — | — | 0.20 | 0.40 |
| Cocamidopropyl Dimethylamine[8] | — | — | 0.20 | 0.50 | — | — | — | — | — |
| Stearamidopropyl Dimethylamine[9] | — | — | — | — | 0.20 | 0.20 | — | — | — |
| pH | 5.16 | 4.94 | 5.01 | 5.09 | 5.14 | 4.94 | 5.29 | 4.99 | 5.22 |

[1] 50% aqueous solution; if necessary, a second addition of the 50% citric acid solution was made after all the ingredients were incorporated into the composition to adjust the pH to between 2.5 and less than 7;
[2] Included in the composition as a 28% active solution in an amount of 35% by weight as is;
[3] Included in the composition as a 26% active solution in an amount of 35% by weight as is;
[4] VARION CAS, Sherex Chemical Co., Dublin, OH; included in the composition as a 50% active solution in an amount of 3.5% by weight as is;
[5] Preservative, methylchloroisothiazoline and methylisothiazoline, available from Rohm and Haas Co., Philadelphia, Pa.;
[6] Preservative, DMDM hydantoin, available from Glyco, Inc., Greenwich, CT;
[7] Polymeric amidoamine compound, available commercially from Sandoz, Inc., East Hanover, NJ as POLYMER AMD; included in the composition as a 40% active solution in an amount of 0.5% (EXS. 1 and 8) or 1% (EX. 9) by weight as is;
[8] Monomeric amidoamine compound, available commercially from Inolex Chem. Co., Philadelphia, PA as LEXAMINE C-13; included in the composition as a 100% active ingredient; and
[9] Monomeric amidoamine compound, available commercially from Inolex Chem. Co., Philadelphia, PA as LEXAMINE S-13; included in the composition as a 100% active ingredient.

The compositions of EXS. 1 through 9 were prepared to compare compositions of the present invention (EXS. 2, 8 and 9) to shampoo compositions absent a conditioning agent (EXS. 1 and 7) and to shampoo-conditioner compositions (EXS. 3 and 6) including monomeric amidoamine compounds that are known hair conditioners. In particular, compositions of EXS. 3 through 6 include either LEXAMINE C-13 or LEXAMINE S-13 as the monomeric amidoamine compound. These known conditioning compounds are illustrated below in structural formulas (III) and (IV) respectively.

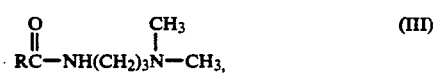

wherein RC— represents the coconut acid radical

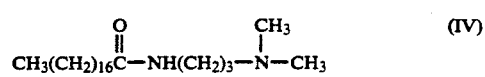

The amine nitrogen atom of compounds (III) and (IV) are protonated at an acidic pH to provide a cationic, acid-neutralized monomeric amidoamine compound that is substantive to the hair. Acid-neutralized monomeric compounds having a structure such as (III) or (IV) have demonstrated an ability to impart conditioning properties to hair. However, such acid-neutralized monomeric amidoamine compounds have substantially reduced the level and stability of the foam generated by an anionic cleansing surfactant when the acid-neutralized monomeric amidoamine is incorporated into a hair shampoo-conditioner composition.

The monomeric amidoamine compounds, as exemplified by the compounds of structural formulas (III) and (IV), have been incorporated into shampoo compositions and have imparted light to moderate conditioning properties to shampooed hair. If increased hair conditioning is desired, an increased amount of the monomeric amidoamine compound is added to the composition. However, although increasing the amount of the monomeric amidoamine compound in the composition improves the conditioning properties of the shampooed hair, the foaming properties of the composition then are further decreased. Therefore, the prior art teaches that both good conditioning and good foaming properties cannot be achieved from a shampoo including an amidoamine compound.

Surprisingly, a polymeric amidoamine compound, as depicted in general structural formula (I) and particularly in structural formula (II), imparts hair conditioning properties to shampooed hair, but does not adversely affect the foam generating properties of an anionic cleansing surfactant. Accordingly, a combination of a polymeric amidoamine of general structural formula (I) and an anionic cleansing surfactant provides an improved hair shampoo-conditioner composition that effectively cleanses the hair; that effectively conditions the hair; and that provides enhanced esthetic properties for greater consumer acceptance, such as the generation of a thick, stable foam and the absence of a greasy or slimy feel upon application to the hair. The excellent cleansing, conditioning and foaming characteristics are observed in hair treated with a shampoo-conditioner composition of the present invention including a low level of the polymeric amidoamine compound of general structural formula (I), such as from about 0.1% to about 2.5% by weight of the composition. In addition, it also has been found that increasing the level of the polymeric amidoamine compound above about 2.5% by weight of the composition does not decrease the foaming characteristics or further appreciably improve the conditioning properties imparted to the shampooed hair.

To demonstrate the improved ability of a shampoo-conditioner of the present invention to provide a copious, stable foam that consumers equate with composition effectiveness, the compositions of EXS. 1 through 9 were tested for an ability to generate and maintain a lather. Specifically, the composition of each Example was tested by adding 0.25 cc (cubic centimeters) of the composition to 100 ml (milliliter) of water having a temperature in the range of 95° F. to 105° F. in a stoppered, 500 ml graduated cylinder. After placing the stopper on the graduated cylinder, the stoppered cylinder, including the composition and the water, was shaken uniformly by hand for ten shakes. The top level of the foam layer was recorded and the top level of the liquid layer was recorded 15 seconds after shaking and again 5 minutes after shaking. The difference between the top level of the foam layer and the top level of the liquid layer is calculated to provide the foam volume after 15 seconds and after 5 minutes. TABLE I summarizes the results of the foam volume tests performed on the compositions of Examples 1 through 9. The tabulated results represent the average value of three replicate foam volume tests for each composition. As will be discussed more fully hereinafter, TABLE I also summarizes the results of a subjective combing index test performed on hair tresses treated with the compositions of EXS. 1 through 9.

TABLE I

FOAM VOLUME AND COMBING INDEX

| EXAMPLE NUMBER | CONDITIONING INGREDIENT | % OF CONDITIONING INGREDIENT | FOAM VOLUME 15 SEC. | FOAM VOLUME 5 MIN. | COMBING INDEX |
|---|---|---|---|---|---|
| 1 | NONE | 0 | 300 | 257 | 1.0 |
| 2 | POLYMER AMD | 0.2 | 298 | 273 | 5.0 |
| 3 | LEXAMINE C-13 | 0.2 | 270 | 230 | 2.0 |
| 4 | LEXAMINE C-13 | 0.5 | 222 | 198 | 2.5 |
| 5 | LEXAMINE S-13 | 0.2 | 262 | 218 | 2.0 |
| 6 | LEXAMINE S-13 | 0.5 | 187 | 160 | 3.0 |
| 7 | NONE | 0 | 255 | 215 | 1.0 |
| 8 | POLYMER AMD | 0.2 | 255 | 221 | 4.5 |
| 9 | POLYMER AMD | 0.4 | 242 | 215 | 4.5 |

The foam volume data tabulated in TABLE I demonstrate that hair shampoo-conditioner compositions of the present invention including 0.2% by weight of the polymeric amidoamine compound (EXS. 2 and 8) generate essentially the same initial foam volume as a hair shampoo composition absent a conditioning agent (EXS. 1 and 7). The compositions of EXS. 1 and 7 are typical hair shampoo compositions that generate an intial foam acceptable to consumers, i.e. 300 ml and 255 ml respectively. The compositions of Examples 1 and 7 differ only in the identity of the anionic cleansing surfactant, therefore, accounting for the difference in foam volume between the composition of EX. 1 and the composition of EX. 7. Unexpectedly, the compositions of EXS. 2 and 8, including 0.2% by weight of the polymeric amidoamine depicted in structural formula (II), generated an essentially identical foam level as the compositions of EXS. 1 and 7. In contrast, the compositions of EXS. 3 and 5, including 0.2% by weight of a monomeric amidoamine compound demonstrated an approximately 10% decrease in initial foam generation, i.e. 270 ml and 262 ml for EXS. 3 and 5 respectively compared to 300 ml for EX. 1. In addition, increasing the amount of monomeric amidoamine compound to 0.5% by weight in the compositions of EXS. 4 and 6 further substantially reduced the initial foam volume to a total decrease in initial foam of about 25% for EX. 4 (222 ml) and about 38% for EX. 6 (187 ml) compared to EX. 1 (300 ml). In contrast, increasing the level of the polymeric amidoamine compound in the composition of EX.

9 to 0.4% by weight reduced the initial foam volume by only about 5% compared to EX. 7, i.e. 242 ml compared to 255 ml. Therefore, it has been shown that including up to about 0.4% by weight of an polymeric amidoamine compound of general structural formula (I) into a shampoo-conditioner composition essentially does not adversely affect the initial foam volume generated by the composition, whereas adding 0.2% by weight of a monomeric amidoamine compound has a substantial adverse affect on the initial foam volume generated by the composition.

The data summarized in TABLE I also show that the foam volume generated by a composition of the present invention is stable. After 5 minutes, the foam generated by the shampoo composition of EX. 1 has decreased from 300 ml to 257 ml, or 43 ml (14%), whereas the foam generated by the composition of EX. 2 has decreased from 298 ml to 273 ml, or 25 ml (8%), for a surprising 42% improvement in foam volume stability after 5 minutes. The prior art, however, teaches that an amidoamine compound should provide a lower foam volume after 5 minutes as opposed to a greater foam volume. This prior art teaching is demonstrated in the foam volume tests for the compositions of EXS. 3 through 6, each including a monomeric amidoamine compound, and each demonstrating a substantially decreased foam volume after 5 minutes compared to the composition of EX. 1 absent a conditioning compound and the composition of EX. 2 including a polymeric amidoamine compound. Similarly, the composition of EX. 9 demonstrates a 5 min. foam volume as stable as the 5 min. foam volume of the composition of EX. 7 that is absent a conditioning compound; and the composition of EX. 8 demonstrates a more stable 5 min. foam than the 5 min. foam volume of the composition of EX. 7.

The generation of a copious and stable foam, as illustrated in TABLE I for the compositions of EXS. 2, 8 and 9 is important because consumers are accustomed to, and expect, a shampoo product to produce a copious and rich foam. If the shampoo does not generate a sufficient foam, a consumer concludes that the shampoo product is inferior. Accordingly, prior investigators have found it necessary to increase the amount of anionic surfactant in the composition to offset the foam-reducing effects of the conditioner compound. Although the increased level of anionic surfactant can generate an acceptable foam volume, other product disadvantages then become apparent. For example, the cost of the shampoo product is increased unnecessarily because the excess anionic cleansing surfactant is added only to provide a sufficient foam volume to satisfy consumer expectations and does not provide further enhanced cleansing. The excess amount of anionic surfactant simply is rinsed from the shampooed hair and therefore is wasted. More importantly, the increased amount of anionic surfactant in the composition may solubilize the polymeric amidoamine compound to such an extent that the polymeric amidoamine compound does not sufficiently deposit on the hair shaft, and therefore is rinsed from the hair with the anionic surfactant. Accordingly, the hair shampoo-conditioner composition does not impart sufficient conditioning properties to the hair.

To further demonstrate the ability of a composition of the present invention to cleanse and condition hair, the compositions of Examples 1 through 9 were tested to determine the relative ability of the compositions of EXS. 1 through 9 to effectively clean hair and to simultaneously impart conditioning properties to hair during shampooing. In particular, to show that a composition of the present invention effectively cleanses the hair and imparts superior hair conditioning properties to hair, hair treated with a composition of Example 2, 8 or 9 was compared to hair treated with a composition of Example 1 or a composition of Example 3 through 7. Specifically, the compositions of EXS. 2, 8 and 9 were tested for their ability to cleanse the hair and to impart wet combing conditioning properties to the shampooed hair.

In a standard salon test to determine the combing index of shampooed hair, a clean and dry 50% gray hair tress, available from DeMeo Bros., NY, N.Y., weighing 2 grams and having a length of six inches, first was wetted thoroughly with tap water having a temperature of about 100° F. Then about 0.5 cc of a composition of EXS. 1 through 9 was applied to the wetted tress, and the tress was shampooed for one minute. Then, the shampooed tress was rinsed with warm tap water for 30 seconds. The rinsed tress first was combed with a large-toothed comb to detangle the hair, and finally with a small-toothed comb to determine the ease of combing, or combing index. In this salon test, laboratory panelists combed through the wet, treated hair tresses and ranked the hair tresses treated identically by a composition of EXS. 1 through 9 for ease of wet combing.

The shampooed hair was rated in a blind test for one or more hair-conditioning properties, like combing index, by a trained judge in a subjective ranking of 1 unit (worst) to 5 units (best). Then, the ratings of the judges for a particular hair conditioning property were averaged. A difference in rating of at least 0.3 units is considered a significant difference for that particular hair-conditioning property. The trained judges can rate the shampoo and the shampooed hair for shampooing and hair conditioning properties such as ease of application, foam volume, foaming speed, detangling, drying difficulty, fragrance, ease of rinsing, wet feel, wet comb, residue, dry combing, dry feel, coating, flakes/dust, static manageability, condition of ends, sheen/luster, body, effect of hair color, irritation and overall condition.

From the data summarized in TABLE I, it was observed that a hair tress treated with a composition of EX. 1 or EX. 7 exhibited a very poor combing index of 1.0. Such a poor combing index is expected for a shampoo composition absent a conditioning agent. It also was observed that a hair tress treated with a composition of EXS. 3 through 6, including a prior art monomeric amidoamine conditioning agent, exhibited combing indices of 2.0 to 3.0. Again, the improved combing indices over hair-treated with a composition of EXS. 1 or 7 was expected because a known conditioning compound was included in the shampoo composition. However, surprisingly and unexpectedly, a hair tress treated with a composition of the present invention (EX. 2), including a polymeric amidoamine having structural formula (II), exhibited an exceptional combing index of 5.0. It also should be noted that the composition of EX. 2, including 0.2% by weight of the polymeric amidoamine, significantly outperformed the compositions of EXS. 4 and 6 that include 0.5% by weight of a prior art monomeric amidoamine.

Accordingly, it has been found that a composition of the present invention generates an excellent initial foam and exhibits an improved foam stability, plus imparts an unexpectedly and substantially improved combing index. Furthermore, the present composition demonstrates such improved properties even though a polymeric amidoamine of general structural formula (I) is included in the composition at levels lower than prior art conditioning agents. The compositions of EXS. 7 through 9 show that increasing the level of the polymeric amidoamine compound does not adversely affect either the foaming properties of the composition or the conditioning properties the composition imparts to the hair. Therefore, increased levels of the polymeric amidoamine compound can be included in the composition to improve composition performance and esthetics. It has been found however, that amounts by weight of the polymeric amidoamine compound in the composition above about 2.5% do not further improve composition performance or esthetics, and therefore, amounts of polymeric amidoamine compound in excess of about 2.5% by weight are wasted. It also should be noted that the compositions of EX. 2 and EX. 8 utilize different anionic surfactants, and that the polymeric amidoamine did not adversely affect foam generation of either anionic surfactant-based composition and that the polymeric amidoamine compound still imparted excellent wet combing properties to the hair, i.e. combing indices of 5.0 and 4.5 for hair treated with the compositions of EXS. 2 and 8, respectively.

Overall, the above tests demonstrate that a composition of the present invention, including an anionic cleansing surfactant and a polymeric amidoamine conditioning compound, surprisingly and unexpectedly provides a hair shampoo-conditioner composition that exhibits an extended shelf stability, that generates a copious and stable foam, that effectively cleanses the hair, and that imparts unexpectedly improved hair-conditioning properties to hair during shampooing.

To show that a composition of the present invention is capable of generating a copious and stable foam volume at a pH in the range of about 2.5 to less than 7, the following composition of Example 10 was prepared by admixing the ingredients in the listed order. After preparing the composition of Example 10, the pH was adjusted by adding a sufficient amount of the citric acid solution to decrease the pH, or a sufficient amount of a sodium hydroxide solution to increase the pH, to provide the compositions of Examples 10A through 10E. The compositions of Examples 10A through 10E then were tested for an ability to generate a stable and copious foam by performing a foam volume test as described above. The test results are summarized in TABLE II.

| Ingredient | % by weight (added as is) | % by weight of ingredient present in the composition |
| --- | --- | --- |
| Water, deionized | 52.40 | q.s. |
| Citric Acid (50% aqueous solution) | 0.20 | q.s. to pH about _ |
| Sodium Laureth-2 Sulfate (26% active) | 40.00 | 10.40 |
| Cocamide DEA (100% active) | 4.00 | 4.00 |
| DMDM Hydantoin | 0.10 | 0.10 |
| Sodium Chloride | 1.30 | 1.30 |
| Adipic Acid/ Diethylenetriamine Copolymer (40% active) | 2.00 | 0.80 |

TABLE II
Effect of pH on Composition Compatability and Foam Volume
(Compositions of Example 10)

| | | Composition | Foam Volume | |
| --- | --- | --- | --- | --- |
| | pH | Appearance | 15 sec. | 5 min. |
| EX. 10A | 4.3 | Hazy | — | — |
| EX. 10B | 5.0 | Clear | 240 | 195 |
| EX. 10C | 7.0 | Clear | 240 | 205 |
| EX. 10D | 9.0 | Clear | 235 | 205 |
| EX. 10E | 11.0 | Clear | 225 | 190 |

The data illustrated in TABLE II show that at a pH of 4.3, a composition including 0.8% of a polymeric amidoamine compound is hazy and is incapable of generating a sufficient foam volume for a consumer-acceptable hair shampoo-conditioner composition. However, the data also show that at pH of from above 4.3, to a pH of 11, that a satisfactory foam volume is generated initially (i.e., 15 sec. foam volume test) and that the foam volume is stable (i.e., the 5 min. foam volume test). However, as stated previously, although a stable and copious foam is generated at a pH of about 11, a hair shampoo-conditioner composition of the present invention preferably is maintained in a pH range of from about 2.5 to less than 7 to provide a composition that is sufficiently mild to the hair, skin and eyes of the consumer, and to maximize the conditioning properties imparted to the hair. Furthermore, as will be demonstrated more fully hereinafter, compositions including a lesser amount of the polymeric amidoamine compound are clear and generate a sufficient foam volume having a sufficient stability at pH values as low as about 2.5.

It also should be noted that the composition of Example 10B, including 0.8% by weight of the polymeric amidoamine compound and having a pH of 5, generates a foam volume that is essentially equivalent to the foam volume generated by the composition of Example 9, including 0.4% by weight of the polymeric amidoamine compound and having a pH of 5.22. Therefore, unlike the prior art monomeric amidoamines, increasing the amount of the polymeric amidoamine compound in the hair shampoo-conditioner composition does not adversely affect the ability of the composition to generate an acceptable foam volume.

It also was found that the minimum pH required to obtain a clear composition is related to the amount of polymeric amidoamine compound present in the composition. In particular, to provide a clear composition the pH of the composition is increased, up to a pH of less than 7, as the amount of polymeric amidoamine compound in the composition is increased. TABLE III and FIG. 1 illustrate that as the amount of polymeric amidoamine compound in the composition of Example 11 increases from 0.4% to 2.4%, that the minimum pH necessary to achieve a clear composition increases from about 2.5 to about 7. Therefore, in order to achieve a clear composition that is capable of generating a stable and copious foam volume, the minimum pH is related to the amount of polymeric amidoamine compound present in the composition. From TABLE III and FIG. 1, it is seen that in range wherein the polymeric amidoamine compound is included in the composition, i.e. from about 0.2% to about 2.5% by weight, a composition pH in the range of from about 2.5 to less than 7 provides a clear shampoo-conditioner composition. Example 11H shows that a pH of greater than 7 is necessary to provide a clear solution when the amount of polymeric amidoamine compound in the composition is greater than 2.5%.

EXAMPLE 11

| Ingredient | % by weight (added as is) | % by weight of ingredient present in the composition |
|---|---|---|
| Water, deionized | q.s. | q.s. |
| Citric Acid (50% aqueous solution) | 0.20 | q.s. until composition is clear[1] |
| Sodium Laureth-2 Sulfate (26% active) | 40.00 | 10.40 |
| Cocamide DEA (100% active) | 4.00 | 4.00 |
| DMDM Hydantoin | 0.10 | 0.10 |
| Sodium Chloride | 1.30 | 1.30 |
| Adipic Acid/ Diethylenetriamine Copolymer (40% active) | varies from 1 to 7 | varies from 0.4 to 2.8 |

[1])Sodium hydroxide solution is added to increase the pH to achieve clarity.

TABLE III

| Composition pH to Achieve a Clear Composition | | |
|---|---|---|
| | % Polymeric Conditioning Compound | pH |
| EX. 11A | 0.4% | 2.50 |
| EX. 11B | 0.8% | 4.30 |
| EX. 11C | 1.2% | 4.83 |
| EX. 11D | 1.6% | 5.30 |
| EX. 11E | 1.8% | 5.56 |
| EX. 11F | 2.0% | 5.94 |
| EX. 11G | 2.4% | 6.99 |
| EX. 11H | 2.8% | 7.84 |

To further demonstrate the ability of a composition of the present invention to impart conditioning properties to shampooed hair, compositions prepared according to formulation of EX. 11, and including from 0% to 2.4% polymeric amidoamine compound, were applied to human hair, and the shampooed hair, both wet and dry, was subjected to an Instron combing study. An Instron combing study measures the energy required to comb through a hair tress to compare the energy required to comb through an untreated tress to the energy required to comb through a tress treated with a composition of the present invention.

In general, the hair shampoo-conditioner compositions were tested by applying about one milliliter, or about one gram, of the composition to clean, wet, naturally dark brown tresses of normal virgin human hair available commercially from DeMeo Brothers, New York, N.Y. The six inch hair tresses, each weighing two grams, were attached to a plastic tab at the root end. In each test, the composition was combed through the hair and allowed to contact the hair for from 15 seconds to 2 minutes. The hair was rinsed with 32° C. tap water for 30 seconds. The combing test was conducted on either a wet treated tress or a treated tress dried with a blow dryer, as required by the particular combing test.

Figure 2:
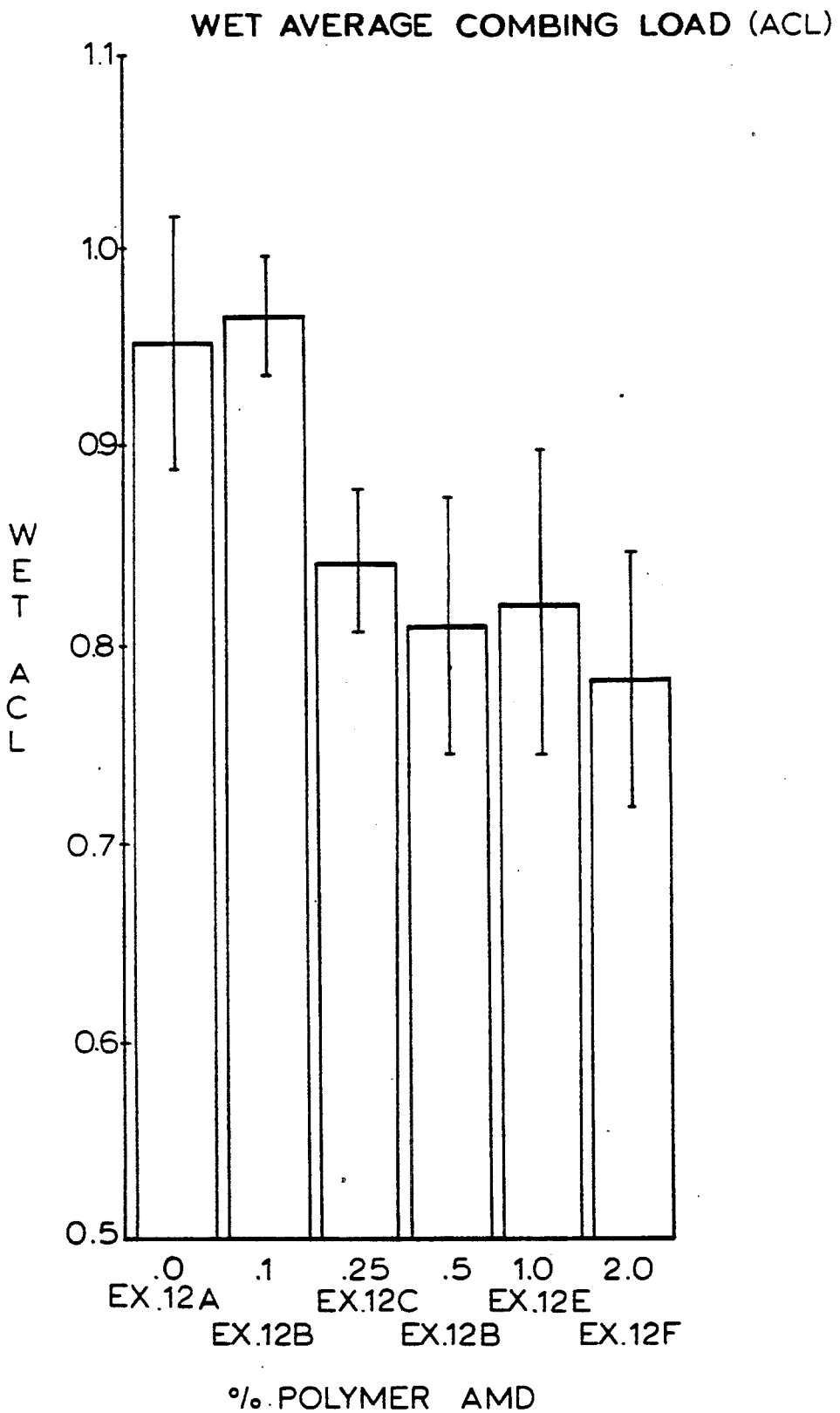
FIG. 2 is a bar graph showing the average combing load for a wet hair tress treated with a hair shampoo-conditioner composition including a varying amount of a polymeric amidoamine compound.

For example, FIG. 2 and TABLE IV illustrate the performance results obtained for the Instron combing test on wet tresses treated by hair shampoo-conditioner compositions including from 0% to 2.4% polymeric amidoamine compound, i.e. Examples 12A through 12I in TABLE IV. The Instron combing test measures the force needed to comb through a wet, treated hair tress.

First, an untreated, wet hair tress is tested and assigned an index value of one.

TABLE IV

| INSTRON AVERAGE COMBING LOAD (ACL) INDEX | | | | |
|---|---|---|---|---|
| | % POLYMER AMD (40% Active) | % Polymeric Amidoamine | pH | Appearance |
| EX. 12A | 0 | 0 | 5.842 | clear |
| EX. 12B | 0.10 | 0.04 | 5.552 | clear |
| EX. 12C | 0.25 | 0.10 | 5.570 | clear |
| EX. 12D | 0.50 | 0.20 | 5.657 | clear |
| EX. 12E | 1.00 | 0.40 | 5.679 | clear |
| EX. 12F | 2.00 | 0.80 | 5.679 | clear |
| EX. 12G | 4.00 | 1.60 | 5.505 | clear |
| EX. 12H | 6.00 | 2.40 | 6.989 | clear |
| EX. 12I | 6.00 | 2.40 | 5.590 | hazy |
| | ACL[1] Wet | | ACL Dry | |
| EX. 12A | 1.0291 | | 0.8910 | |
| EX. 12B | 0.9970 | | 0.9726 | |
| EX. 12C | 0.8782 | | 0.8870 | |
| EX. 12D | 0.8751 | | 0.8765 | |
| EX. 12E | 0.8988 | | 0.9346 | |
| EX. 12F | 0.8414 | | 0.9341 | |
| EX. 12G | 0.8815 | | 0.6601 | |
| EX. 12H | 0.7884 | | 0.6965 | |
| EX. 12I | 0.8789 | | 0.8488 | |

[1])Average combing load

Then a treated wet hair tress is tested, and if the treated hair tress exhibits an index value of less than one, then less energy is required to comb through the treated tress than the untreated tress. Therefore, the lower index value, the easier it is to comb the hair, i.e. the hair is more conditioned.

Accordingly, the bar graph of FIG. 2 and TABLE IV show that a composition including 0% polymeric amidoamine compound (EX. 12A) demonstrates an Instron average wet combing load of about one, and therefore requires about the same energy to comb as an untreated tress. Each bar of the graph represents the mean value of replicate tests, and the vertical line through the top of each bar represents the standard deviation of the replicate tests. Similarly, hair treated with the composition of EX. 12B, including about 0.04% polymeric amidoamine compound, required about the same energy to comb as an untreated tress. However, hair treated with the compositions of EXS. 12C through 12I each required substantially less energy to comb than an untreated hair tress. Therefore, a composition of the present invention, including from about 0.1% to about 2.5% of a polymeric amidoamine compound, demonstrates an ability to improve the wet combing properties of shampooed hair. Surprisingly, the compositions also exhibited a sufficient and stable foam and the compositions satisfactorily cleansed the hair tress.

The data in TABLE IV also show that improved wet combing properties are observed on hair treated with a composition including up to about 2.5% by weight of a polymeric amidoamine compound. A composition including more than about 2.5% by weight of a polymeric amidoamine compound did not further improve the wet combing properties of the treated hair. In addition, it was observed that a clear composition of the present invention imparts more improved wet combing properties than a hazy composition of the present invention. As previously discussed, the clarity of the composition is achieved by providing a sufficiently high pH, but less than 7, for the amount of polymeric amidoamine compound present in the composition. For example, the compositions of EXS. 12H and 12I are identical, with each composition including 2.4% by weight polymeric amidoamine compound. However, the composition of EX. 12H, having a pH of 6.99 is clear, whereas the composition of EX. 12H, having a pH of 5.59, is hazy. Both compositions improved the wet combing properties of treated hair, however the clear composition of EX. 12H substantially outperformed the hazy composition of EX. 12I. In addition, the clear composition of EX. 12H demonstrated a greater and more stable foam volume. Accordingly, it is preferred that a composition of the present invention is a clear composition. However, improved hair conditioning properties nevertheless are observed when the hair is shampooed with hazy composition.

Figure 3:
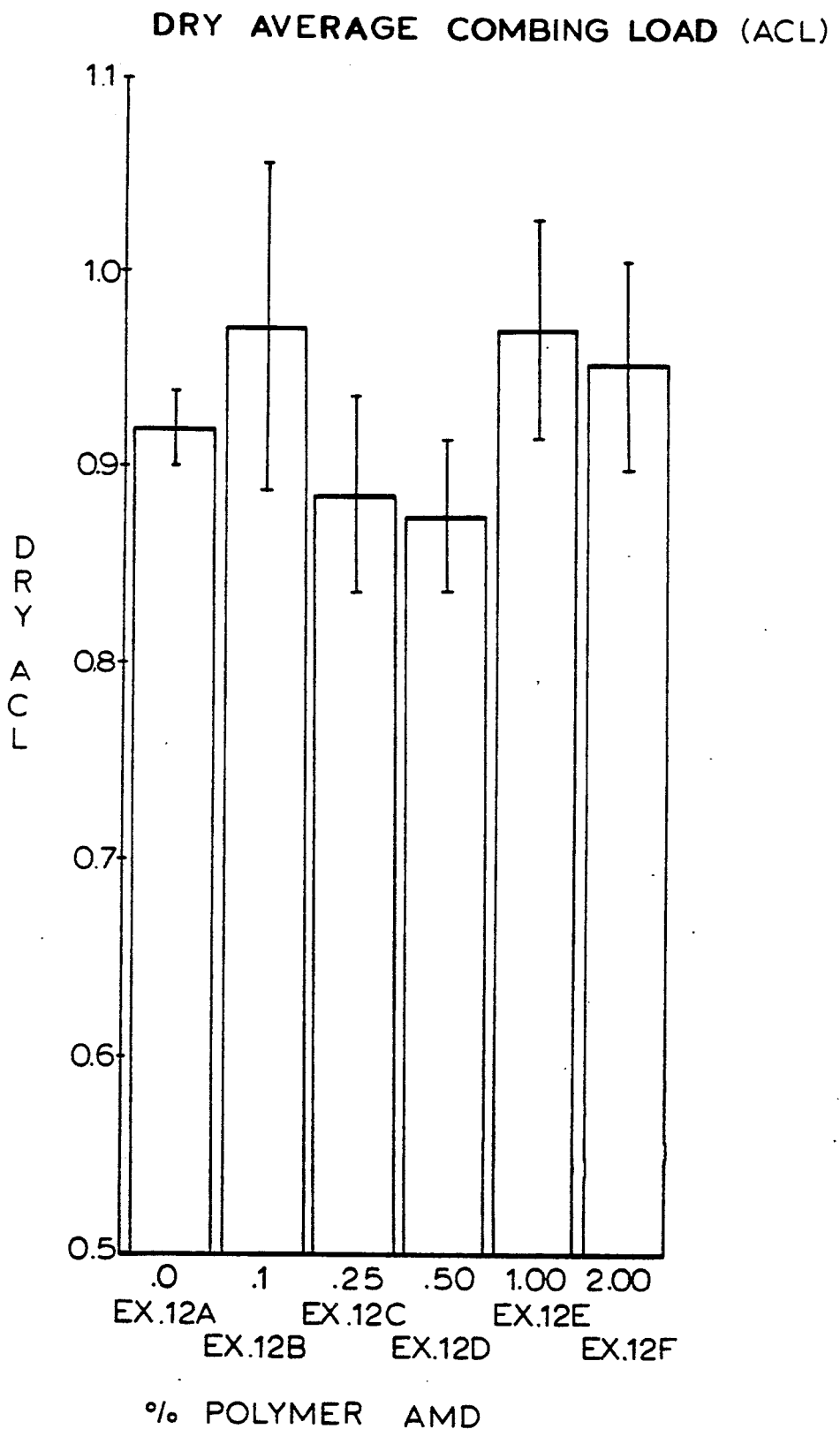
FIG. 3 is a bar graph showing the average combing load for a dry hair tress treated with a hair shampoo-conditioner composition including a varying amount of a polymeric amidoamine compound.

FIG. 3 and TABLE IV demonstrate similar results for the dry combing Instron combing test. Dry hair tresses treated with a composition of the present invention, i.e. EXS. 12C through 12I, generally required less energy to comb than a dry tress that was untreated, i.e. the combing load is less than one. In addition, the dry combing load was substantially improved for tresses treated with the compositions of EX 12G and EX. 12H, including 1.6% and 2.4% of the polymeric amidoamine compound respectively. A comparison of a hair tress treated with the composition of 12H to a hair tress treated with the composition of EX. 12I showed that a clear composition outperforms a hazy composition.

To further demonstrate the unexpected results achieved by the hair shampoo conditioner composition of the present invention, including a polymeric amidoamine compound of general structural formula (I), a related polymeric amidoamine, having the CTFA designation of adipic acid/dimethylaminohydroxy propyl diethylenetriamine copolymer, and depicted by structural formula (V):

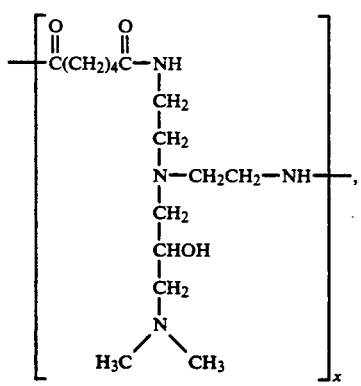

(V)

was tested for its ability to condition hair and generate an acceptable foam volume when incorporated into a hair shampoo-conditioner composition. The polymeric amidoamine compound of structural formula (V) is available commercially from Sandoz, Inc, East Hanover, N.J., as CARTARETIN F-4 or CARTARETIN F-23. The CARTARETIN products are known hair conditioners and were used by Homma et al. in U.S. Pat. No. 4,381,259, in conjunction with an anionic surfactant and an anionic phosphate ester, to cleanse and condition the hair.

Accordingly, the composition of Example 13 was prepared by admixing the ingredients in the listed order. After preparing the composition of Example 13, the pH of the composition was adjusted over the range of from about 4.9 to about 6.7 by the addition of a sufficient amount of a sodium hydroxide solution to provide the compositions of Examples 13A through 13F.

EXAMPLE 13

| Ingredient | % by weight (added as is)* | % by weight of ingredient present in the composition |
|---|---|---|
| Water, deionized | 51.73 | q.s. |
| Citric Acid (50% aqueous solution) | 0.20 | q.s. to pH about _ |
| Sodium Laureth-2 Sulfate (26% active) | 40.00 | 10.40 |
| Cocamide DEA (100% active) | 4.00 | 4.00 |
| DMDM Hydantoin | 0.10 | 0.10 |
| Sodium Chloride | 1.30 | 1.30 |
| Adipic Acid/ Dimethylaminohydroxy propyl Diethylenetriamine Copolymer (30% active)[1] | 2.67 | 0.80 |

[1]CARTARETIN F-4, Sandoz, Inc., East Hanover, N.J.

The data presented in TABLE V illustrate that hair shampoo-conditioner composition including a polymeric amidoamine compound of general structural formula (V) is not stable at a pH of below about 6, whereas the polymeric amidoamine compound utilized in the present invention, i.e. a compound of general structural formula (I), is compatible in the hair shampoo-conditioner down to the pH of about 2.5

TABLE V

EFFECT OF COMPOSITION PH ON COMPOSITION COMPATIBILITY (COMPOSITION OF EX. 13)

| | pH | Composition Appearance |
|---|---|---|
| EX. 13A | 4.887 | Hazy |
| EX. 13B | 5.201 | Hazy |
| EX. 13C | 5.740 | Hazy |
| EX. 13D | 5.954 | Slightly Hazy |
| EX. 13E | 6.117 | Clear |
| EX. 13F | 6.654 | Clear | included an anionic phosphate ester in the hair shampoo-conditioner composition to effectively incorporate the CARTARETIN F-4 into the composition. Therefore, surprisingly, a polymeric amidoamine compound of general structural formula (I) is compatible in the present hair shampoo-conditioner composition over the pH range of from about 2.5 to less than 7, whereas the related polymeric amidoamine compound of general structural formula (V) is compatible in the hair shampoo-conditioner composition only at a pH range of about 6 or greater.

Accordingly, the method and composition of the present invention cleanse the hair and impart physical and cosmetic conditioning properties to hair during shampooing that usually are observed only by treating the hair sequentially, first with a hair shampoo composition, then with a hair conditioning composition. It is both surprising and unexpected for a composition of the present invention, having a pH in the range of from about 2.5 to less than 7 and including an anionic cleansing surfactant and a polymeric conditioning compound, to demonstrate such an excellent storage stability, to generate a foam volume normally exhibited by a hair shampoo composition absent a conditioning agent, to effectively cleanse the hair and to sufficiently deposit the polymeric conditioning compound on the hair to impart such a high degree of conditioning to the shampooed hair.

In addition, the method and composition of the present invention overcome many of the disadvantages of prior hair shampoo-conditioner compositions and provide the further benefits of not leaving the hair tacky or sticky; not leaving the hair with an oily or greasy appearance; not forming a crust and therefore providing compatibility; and providing manageable and styleable hair having body. In addition, after shampooing the hair feels natural and thickened, has body, and is soft, shiny and manageable.

Obviously, many modifications and variations of the invention as hereinbefor set forth can be made without departing from the spirit and scope thereof, and therefore only such limitations should be imposed as are indicated by the appended claims.

We claim:

1. A hair shampoo-conditioner composition consisting essentially of:
   (a) from about 1% to about 20% by weight of an anionic cleansing surfactant;
   (b) from about 0.1% to about 2.5% by weight of a substantially uncrosslinked polymeric amidoamine having the formula:

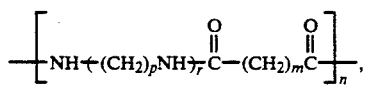

wherein n is a number in the range of from two to about 1000, m is a number in the range of from one to about 18, and p and r are numbers in the range of from one to about four; and
   (c) a suitable carrier comprising water; wherein the composition has a pH in the range of from about 2.5 to less than 7.

2. The composition of claim 1 wherein the anionic cleansing surfactant is present in an amount ranging from about 3% to about 15% by weight of the composition.

3. The composition of claim 1 wherein the anionic cleansing surfactant is present in an amount ranging from about 7% to about 12% by weight of the composition.

4. The composition of claim 1 wherein the anionic cleansing surfactant is selected from the group consisting of sodium lauryl sulfate, ammonium lauryl sulfate, sodium lauryl ether sulfate, ammonium lauryl ether sulfate and combinations thereof.

5. The composition of claim 1 wherein the polymeric amidoamine compound is present in an amount ranging from about 0.15% to about 2% by weight of the composition.

6. The composition of claim 1 wherein the polymeric amidoamine compound is present in an amount ranging from about 0.2% to about 1.5% by weight of the composition.

7. The composition of claim 1 wherein the number n is in the range of from 2 to about 500.

8. The composition of claim 1 wherein the number n is in the range of from 2 to about 300.

9. The composition of claim 1 wherein the polymeric amidoamine compound has the structure:

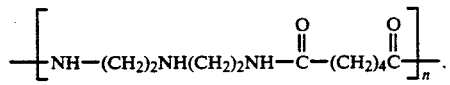

10. The composition of claim 1 wherein the polymeric amidoamine compound has an average molecular weight in the range of from about 240 to about 187,500.

11. The composition of claim 1 wherein the suitable carrier further comprises from 0% to about 5% by weight of the composition of a nonaqueous solvent.

12. The composition of claim 11 wherein the nonaqueous solvent is selected from the group consisting of glycerol, ethylene glycol, propylene glycol, hexylene glycol and combinations thereof.

13. The composition of claim 1 wherein the pH is in the range of from about 2.5 to about 6.

14. The composition of claim 1 wherein the pH is in the range of from about 2.5 to about 5.5.

15. The composition of claim 1 further comprising from about 0% to about 3% by weight of a conditioning agent selected from the group consisting of a fatty alcohol, an ethoxylated fatty alcohol, a propoxylated fatty alcohol and combinations thereof, wherein the fatty alcohol includes from about 12 to about 18 carbon atoms.

16. The composition of claim 15 wherein the conditioning agent is selected from the group consisting of myristyl alcohol, lauryl alcohol, stearyl alcohol, cetaryl alcohol, cetyl alcohol, ethylene glycol cetyl ether, polyoxyethylene(2) stearyl ether, polyoxyethylene(24) cetyl ether and combinations thereof.

17. A hair shampoo-conditioner composition consisting essentially of:
   (a) from about 1% to about 20% by weight of an anionic cleansing surfactant;
   (b) from about 0.1% to about 2.5% by weight of a polymeric amidoamine compound, said polymeric amidoamine compound being substantially uncrosslinked, and having the structure:

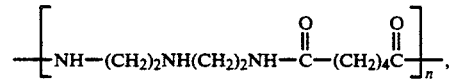

wherein n is a number in the range of from 2 to about 1000; and
   (c) a suitable carrier comprising water; wherein the composition has a pH in the range of from about 2.5 to less than 7.

18. A method of treating hair comprising contacting the hair with a hair shampoo-conditioner composition consisting essentially of:
   (a) from about 1% to about 20% by weight of an anionic cleansing surfactant;
   (b) from about 0.1% to about 2.5% by weight of a substantially uncrosslinked polymeric amidoamine compound having the formula:

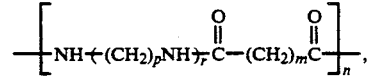

wherein n is a number in the range of from two to about 1000, m is a number in the range of from one to about 18, and p and r are numbers in the range of from one to about four; and (c) a suitable carrier comprising water; wherein the composition has a pH in the range of from about 2.5 to less than 7.

19. The method of claim 18 wherein the polymeric amidoamine compound has the structure

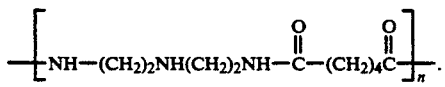

20. A method of cleansing the hair and imparting conditioning properties to the hair comprising contacting the hair for a time sufficient for the hair to interact with a composition consisting essentially of:
   (a) from about 1% to about 20% by weight of an anionic cleansing surfactant;
   (b) from about 0.1% to about 2.5% by weight of a substantially uncrosslinked polymeric amidoamine compound having the formula:

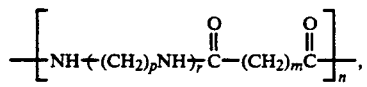

wherein n is a number in the range of from two to about 1000, m is a number in the range of from one to about 18, and p and r are numbers in the range of from one to about four; and
   (c) a suitable carrier comprising water; wherein the composition has a pH in the range of from about 2.5 to less than 7.

21. The method of claim 20 further comprising rinsing the hair with water after contacting the hair with the composition.

22. A method of cleansing the hair and imparting conditioning properties to the hair comprising contacting the hair for a time sufficient for the hair to interact with a composition consisting essentially of:
   (a) from about 1% to about 20% by weight of an anionic cleansing surfactant;
   (b) from about 0.1% to about 2.5% by weight of a polymeric amidoamine compound, said polymeric amidoamine compound being substantially uncrosslinked, and having the structure:

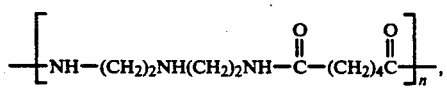

wherein n is a number in the range of from 2 to about 1000; and
   (c) a suitable carrier comprising water; wherein the composition has a pH in the range of from about 2.5 to less than 7.

23. A hair shampoo-conditioner composition consisting essentially of:
   (a) from about 1% to about 20% by weight of an anionic cleansing surfactant;
   (b) from about 0.1% to about 2.5% by weight of a substantially uncrosslinked polymeric amidoamine compound consisting essentially of:
      i) an aromatic dicarboxylic acid selected from the group consisting of phthalic acid, isophthalic acid, terephthalic acid, naphthalene-2,6-dicarboxylic acid, pyridine-2,5-dicarboxylic acid, quinoline-2,4-dicarboxylic acid, o-phenylenediacetic acid, m-phenylenediacetic acid, p-phenylenediacetic acid, homophthalic acid, o-phenylene-$\beta$-propionic acid, and combinations thereof, and
      ii) a polyamine selected from the group consisting of ethylenediamine, diethylenetriamine, triethylenetetramine, dipropylenetriamine, 1,3-diaminopropane, 1,4-diaminobutane, piperazine, and combinations thereof; and
   (c) a suitable carrier comprising water; wherein the composition has a pH in the range of from about 2.5 to less than 7.

24. A method of treating hair comprising contacting the hair with a hair shampoo-conditioner composition consisting essentially of:
   (a) from about 1% to about 20% by weight of an anionic cleansing surfactant;
   (b) from about 0.1% to about 2.5% by weight of a substantially uncrosslinked polymeric amidoamine compound consisting essentially of:
      i) an aromatic dicarboxylic acid selected from the group consisting of phthalic acid, isophthalic acid, terephthalic acid, naphthalene-2,6-dicarboxylic acid, pyridine-2,5-dicarboxylic acid, quinoline-2,4-dicarboxylic acid, o-phenylenediacetic acid, m-phenylenediacetic acid, p-phenylenediacetic acid, homophthalic acid, o-phenylene-$\beta$-propionic acid, and combinations thereof, and
      ii) a polyamine selected from the group consisting of ethylenediamine, diethylenetriamine, triethylenetetramine, dipropylenetriamine, 1,3-diaminopropane, 1,4-diaminobutane, piperazine, and combinations thereof; and
   (c) a suitable carrier comprising water; wherein the composition has a pH in the range of from about 2.5 to less than 7.

25. A hair shampoo-conditioner composition consisting essentially of:
   (a) from about 1% to about 20% by weight of an anionic cleansing surfactant;
   (b) from about 0.1% to about 2.5% by weight of a substantially uncrosslinked polymeric amidoamine having the formula:

wherein n is a number in the range of from two to about 1000, m is a number in the range of from one to about 18, and p and r are numbers in the range of from one to about four;
   (c) from 0% to about 5% by weight of an amphoteric surfactant, from 0% to about 5% by weight of a nonionic surfactant, or a combination thereof; and
   (d) a suitable carrier comprising water; wherein the composition has a pH in the range of from about 2.5 to less than 7.

26. A method of cleansing the hair and imparting conditioning properties to the hair comprising contacting the hair for a time sufficient for the hair to interact with a composition consisting essentially of:

(a) from about 1% to about 20% by weight of an anionic cleansing surfactant;

(b) from about 0.1% to about 2.5% by weight of a substantially uncrosslinked polymeric amidoamine compound having the formula:

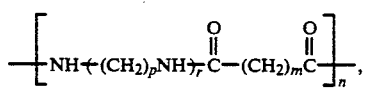

wherein n is a number in the range of from two to about 1000, m is a number in the range of from one to about 18, and p and r are numbers in the range of from one to about four;

(c) from 0% to about 5% by weight of an amphoteric surfactant, from 0% to about 5% by weight of a nonionic surfactant, or a combination thereof; and (d) a suitable carrier comprising water; wherein the composition has a pH in the range of from about 2.5 to less than 7.

* * * * *